(12) United States Patent
Faulks et al.

(10) Patent No.: US 8,518,006 B2
(45) Date of Patent: Aug. 27, 2013

(54) PERSONAL WEAR ABSORBENT ARTICLE WITH TAB

(75) Inventors: Michael J. Faulks, Neenah, WI (US); Robert Lee Popp, Hortonville, WI (US); Michael D. Sperl, Waupaca, WI (US); Nancy Meetz, Appleton, WI (US); Sandra M. Rogers, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1025 days.

(21) Appl. No.: 12/130,601

(22) Filed: May 30, 2008

(65) Prior Publication Data
US 2009/0299318 A1 Dec. 3, 2009

(51) Int. Cl.
*A61F 13/62* (2006.01)
*A61F 13/58* (2006.01)

(52) U.S. Cl.
USPC .............................. 604/385.04; 604/385.03

(58) Field of Classification Search
USPC .................. 604/385.03, 386–387, 389–392
See application file for complete search history.

(56) References Cited

U.S. PATENT DOCUMENTS

| 3,848,594 | A | * | 11/1974 | Buell ........................... 604/390 |
| 4,041,203 | A | | 8/1977 | Brock et al. |
| 4,374,888 | A | | 2/1983 | Bornslaeger |
| 4,581,772 | A | * | 4/1986 | Smith ............................... 2/111 |
| 4,663,220 | A | | 5/1987 | Wisneski et al. |
| 4,766,029 | A | | 8/1988 | Brock et al. |
| 4,846,815 | A | * | 7/1989 | Scripps ........................ 604/391 |
| 4,869,724 | A | * | 9/1989 | Scripps ........................ 604/389 |
| 4,894,060 | A | * | 1/1990 | Nestegard ..................... 604/391 |
| 4,938,753 | A | * | 7/1990 | Van Gompel et al. ... 604/385.29 |
| 4,940,464 | A | | 7/1990 | Van Gompel et al. |
| 4,946,527 | A | * | 8/1990 | Battrell ........................... 156/60 |
| 4,988,346 | A | | 1/1991 | Pfefferkorn |
| 5,019,073 | A | * | 5/1991 | Roessler et al. ............... 604/391 |
| 5,046,272 | A | | 9/1991 | Vogt et al. |
| 5,104,116 | A | | 4/1992 | Pohjola |
| 5,108,384 | A | | 4/1992 | Goulait |

(Continued)

FOREIGN PATENT DOCUMENTS

| EP | 0217032 | 4/1987 |
| EP | 1600132 A1 | 11/2005 |

(Continued)

OTHER PUBLICATIONS

International Search Report & Written Opinion for PCT/IB2009/051784, dated Jan. 5, 2010, 7 pages.

*Primary Examiner* — Susan Su
(74) *Attorney, Agent, or Firm* — Armstrong Teasdale LLP

(57) ABSTRACT

An absorbent article includes a central absorbent assembly having a front waist region, a back waist region, and a crotch region interconnecting the front and back waist regions. Front side panels extend outward from the front waist region and back side panels extend outward from the back waist region. The article includes a pair of tabs. Each tab has an attachment region attached to one of the front side panels and the back side panels, and a tab region extending transversely outward from the attachment region and being releasably attachable to the other one of the front side panels and the back side panels. The one of the front side panels and the back side panels to which the attachment region of the tab is attached has a first stiffness and at least a portion of the tab region has a second stiffness greater than the first stiffness.

20 Claims, 11 Drawing Sheets

(56) References Cited

U.S. PATENT DOCUMENTS

| Number | Type | Date | Name | Ref |
|---|---|---|---|---|
| 5,169,706 | A | 12/1992 | Collier, IV et al. | |
| 5,176,670 | A * | 1/1993 | Roessler et al. | 604/391 |
| 5,176,671 | A * | 1/1993 | Roessler et al. | 604/391 |
| 5,213,881 | A | 5/1993 | Timmons et al. | |
| 5,224,405 | A | 7/1993 | Pohjola | |
| 5,226,992 | A | 7/1993 | Morman | |
| 5,242,436 | A | 9/1993 | Weil et al. | |
| 5,279,604 | A | 1/1994 | Robertson et al. | |
| 5,399,219 | A * | 3/1995 | Roessler et al. | 156/259 |
| 5,403,302 | A * | 4/1995 | Roessler et al. | 604/391 |
| 5,423,789 | A | 6/1995 | Kuen | |
| 5,464,688 | A | 11/1995 | Timmons et al. | |
| 5,531,732 | A | 7/1996 | Wood | |
| 5,554,143 | A * | 9/1996 | Roe et al. | 604/385.3 |
| 5,593,401 | A * | 1/1997 | Sosalla et al. | 604/385.28 |
| 5,605,735 | A * | 2/1997 | Zehner et al. | 428/100 |
| 5,611,789 | A | 3/1997 | Seth | |
| 5,624,428 | A | 4/1997 | Sauer | |
| 5,624,429 | A * | 4/1997 | Long et al. | 604/391 |
| H1674 | H * | 8/1997 | Ames et al. | 604/389 |
| 5,766,389 | A | 6/1998 | Brandon et al. | |
| 5,797,896 | A | 8/1998 | Schmitz | |
| 5,858,515 | A | 1/1999 | Stokes et al. | |
| 6,030,373 | A * | 2/2000 | VanGompel et al. | 604/386 |
| 6,063,066 | A | 5/2000 | Inoue et al. | |
| 6,174,303 | B1 | 1/2001 | Suprise et al. | |
| 6,264,644 | B1 | 7/2001 | Igaue et al. | |
| 6,287,287 | B1 | 9/2001 | Elsberg | |
| 6,302,871 | B1 | 10/2001 | Nakao et al. | |
| 6,322,552 | B1 | 11/2001 | Blenke et al. | |
| 6,371,949 | B1 | 4/2002 | Soga et al. | |
| 6,387,085 | B1 * | 5/2002 | Van Gompel et al. | 604/391 |
| 6,402,731 | B1 | 6/2002 | Suprise et al. | |
| 6,454,752 | B1 | 9/2002 | Huang et al. | |
| 6,491,675 | B1 | 12/2002 | Shimada et al. | |
| 6,508,797 | B1 | 1/2003 | Pozniak et al. | |
| 6,524,293 | B1 * | 2/2003 | Elsberg et al. | 604/385.13 |
| 6,544,242 | B1 | 4/2003 | Kido et al. | |
| 6,551,294 | B1 | 4/2003 | Elsberg et al. | |
| 6,572,601 | B2 | 6/2003 | Suprise et al. | |
| 6,595,977 | B1 | 7/2003 | Luizzi, Jr. et al. | |
| 6,648,866 | B2 | 11/2003 | Magee et al. | |
| 6,682,512 | B2 | 1/2004 | Uitenbroek et al. | |
| 6,736,804 | B1 | 5/2004 | Robertson et al. | |
| 6,849,067 | B2 | 2/2005 | Fletcher et al. | |
| 6,893,426 | B1 | 5/2005 | Popp et al. | |
| 6,916,750 | B2 | 7/2005 | Thomas et al. | |
| 6,932,802 | B2 | 8/2005 | Luizzi, Jr. et al. | |
| 6,945,968 | B2 | 9/2005 | Svensson et al. | |
| 6,972,012 | B1 | 12/2005 | Pozniak et al. | |
| 6,994,697 | B2 | 2/2006 | Shimada et al. | |
| 6,994,698 | B2 * | 2/2006 | Leak et al. | 604/391 |
| 7,018,368 | B2 * | 3/2006 | Van Gompel et al. | 604/385.16 |
| 7,150,730 | B2 | 12/2006 | Hasler et al. | |
| 7,150,733 | B2 | 12/2006 | Yamakawa et al. | |
| 7,156,833 | B2 | 1/2007 | Couture-Dorschner et al. | |
| 7,175,584 | B2 | 2/2007 | Maxton et al. | |
| 7,189,220 | B2 | 3/2007 | Miyoshi et al. | |
| 7,198,621 | B2 | 4/2007 | Moser et al. | |
| 7,201,744 | B2 | 4/2007 | Van Gompel et al. | |
| 7,207,979 | B2 | 4/2007 | Price et al. | |
| 7,211,072 | B2 | 5/2007 | Nawata et al. | |
| 7,473,818 | B2 | 1/2009 | Datta et al. | |
| 7,568,264 | B2 * | 8/2009 | Miyamoto et al. | 24/442 |
| 7,828,784 | B2 * | 11/2010 | Popp et al. | 604/387 |
| 2002/0032427 | A1 | 3/2002 | Schmitz et al. | |
| 2002/0107498 | A1 * | 8/2002 | Kling et al. | 604/392 |
| 2002/0138059 | A1 | 9/2002 | Van Gompel et al. | |
| 2002/0165518 | A1 | 11/2002 | Datta et al. | |
| 2002/0173768 | A1 | 11/2002 | Elsberg et al. | |
| 2003/0153891 | A1 | 8/2003 | Molee | |
| 2004/0122400 | A1 | 6/2004 | Hancock et al. | |
| 2004/0122413 | A1 * | 6/2004 | Roessler et al. | 604/386 |
| 2004/0236301 | A1 | 11/2004 | Wendelstorf et al. | |
| 2005/0027271 | A1 * | 2/2005 | Popp et al. | 604/385.01 |
| 2005/0090793 | A1 | 4/2005 | Winqvist | |
| 2006/0069376 | A1 | 3/2006 | Miller | |
| 2006/0069378 | A1 | 3/2006 | Winkel et al. | |
| 2007/0250029 | A1 * | 10/2007 | Popp et al. | 604/385.13 |
| 2008/0154227 | A1 * | 6/2008 | Andersson et al. | 604/385.22 |

FOREIGN PATENT DOCUMENTS

| | | | |
|---|---|---|---|
| EP | 1829513 | A2 | 9/2007 |
| GB | 2185383 | A * | 7/1987 |
| GB | 2284742 | A * | 6/1995 |
| JP | 8005691 | Y2 | 2/1996 |
| JP | 2003079666 | A | 3/2003 |
| WO | 9746197 | A1 | 12/1997 |
| WO | 0027328 | A1 | 5/2000 |
| WO | 0037009 | | 6/2000 |
| WO | 0188245 | | 11/2001 |

* cited by examiner

PERSONAL WEAR ABSORBENT ARTICLE WITH TAB

BACKGROUND

The present invention relates generally to absorbent articles intended for personal wear, and more particularly to disposable absorbent articles.

Many absorbent articles intended for personal wear, such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs and left in place to absorb insults as well as to contain fecal waste. When the diaper is to be disposed of, the caregiver will sometimes fold the diaper into a more compact configuration and secure the diaper in this configuration using the primary fastening tabs.

Training pants, unlike diapers, typically come pre-assembled in a wear configuration to more closely resemble conventional underpants. In particular, front and back waist regions of such training pants are typically attached either permanently or refastenably (such as by a primary fastening system) to define a wear configuration of the pants having a waist opening and leg openings.

For such articles where the attachment is refastenable, such as diapers and training pants, pop-opens (separation of the fasteners) can sometimes occur as a result of stresses placed on the attachment by movement of the wearer. For training pants, when a refastenable arrangement is used, the pants may be removed without unfastening, thereby also leaving no fasteners for use in holding the pants compact for disposal. Also, because the fastening components are not visible when the pants are worn there is no positive visual awareness provided to the consumer of such refastenability. Where a permanent attachment is used in such training pants, no fastening system is available for retaining the pants in a compact disposal configuration.

The fastening tabs provided on diapers are relatively small in the longitudinal direction of the diapers. Rather, they are typically much longer in the transverse direction because they are used for pulling the back of the diaper around the wearer and fastening to the front of the diaper. The sides of the diaper are relatively short in length (e.g., from waist opening to leg opening) so control of the sides of the diaper is simple using the small (in the longitudinal direction) fastening tabs provided on diapers. The sides of training pants, however, are typically much longer from the waist opening to the leg openings and therefore more difficult to manipulate with a tab as small as those used on diapers.

In addition, the sides of the training pants (e.g., side panels), as mentioned above, are often constructed to be highly flexible to allow freedom of motion of the wearer while maintaining a comfortable fit. However, such flexibility renders the sides of the training pants more difficult to manually manipulate (for refastening alignment, disposal, etc.).

There is a need, therefore, for a disposal fastening system provided on an absorbent article such as training pants for improved resistance to pop-opens, and for securing the article in a compact disposal configuration while providing a sufficient visual awareness to the consumer of the presence of such a fastening system and sufficient operability and use of such a fastening system.

SUMMARY

In one aspect, an absorbent article for personal wear about a wearer's waist generally comprises a central absorbent assembly comprising a liquid permeable inner layer for facing the wearer, an outer layer for facing away from the wearer, an absorbent body disposed therebetween, a front waist region, a back waist region and a crotch region extending longitudinally between and interconnecting the front and back waist regions. A pair of transversely spaced front side panels extends transversely outward from the front waist region. A pair of transversely spaced back side panels extends transversely outward from the back waist region. The back side panels is attached to the front side panels to define a wear configuration of the absorbent article having a waist opening, a pair of leg openings spaced from the waist opening, and transversely opposite sides defined by the front and back side panels and having a length extending from the waist opening to the respective leg opening. The article further comprises a pair of tabs, separate from the attachment between the front and back side panels. Each tab has an attachment region attached to one of the front side panels and the back side panels, and a tab region extending transversely outward from the attachment region and being releasably attachable to the other one of the front side panels and the back side panels. The one of the front side panels and the back side panels to which the attachment region of the tab is attached has a first stiffness and at least a portion of the tab region of the tab has a second stiffness greater than the first stiffness.

In yet another aspect, an absorbent article for personal wear about a wearer's waist generally comprises a liquid permeable bodyside liner for facing the wearer, an outer cover for facing away from the wearer, and an absorbent body disposed between the liner and the outer cover. The article also comprises a front waist region, a back waist region and a crotch region extending longitudinally between and interconnecting the front and back waist regions. A pair of laterally opposite front side panels extends outward from the front waist region. A pair of laterally opposite back side panels extends outward from the back waist region. The back side panels and front side panels cooperatively define respective sides of the article. The sides of the article have a stiffness. A primary fastening system for releasably attaching the side panels extend outward from the front waist region to respective side panels extending outward from the back waist region. A secondary fastening system comprises a tab attached to one side of the article and being at least in part separate from the primary fastening system. The tab has a fastener region selectively attachable to the article. The tab has a stiffness that is greater than the stiffness of the side of the article.

In yet another aspect, an absorbent article for personal wear about a wearer's waist generally comprises a liquid permeable bodyside liner for facing the wearer and having a stiffness, and an outer cover for facing away from the wearer and having a stiffness. An absorbent body is disposed between the liner and the outer cover. A primary fastening system secures the article in a wear configuration having a waist opening and a pair of leg openings spaced from the waist opening. A secondary fastening system comprises a tab attached to the outer cover and being at least in part separate from the primary fastening system. The tab has a fastener region selectively attachable to the article. The tab has a stiffness that is greater than the stiffness of the outer cover.

Other features of the invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
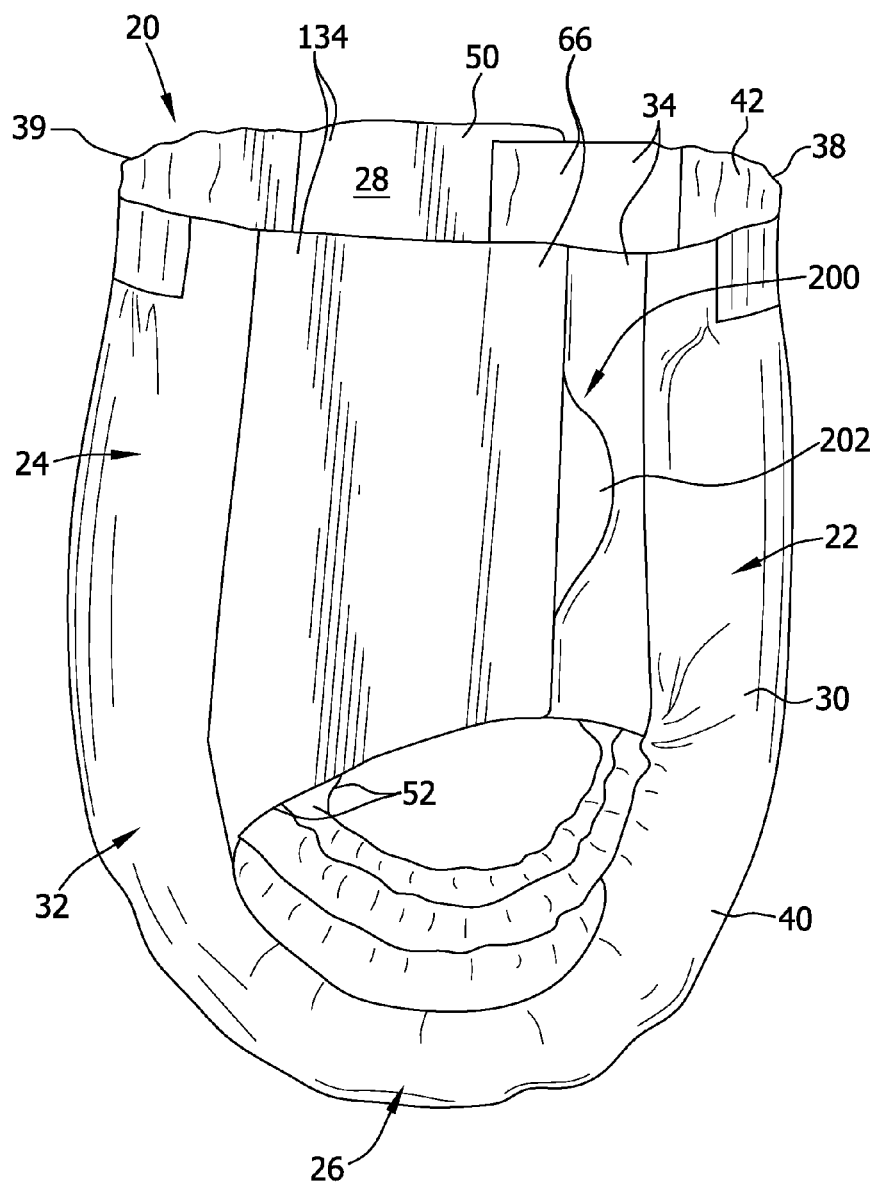
FIG. 1 is a side perspective of one embodiment of a personal wear article in the form of a pair of training pants having a secondary or disposal fastening system illustrated in a fastened condition thereof.

Referring now to the drawings and in particular to FIG. 1, a personal wear absorbent article according to one embodiment is illustrated in the form of a pants-type article for wear about a wearer's waist, and more particularly in the form of children's toilet training pants, indicated in its entirety by the reference numeral 20. The term absorbent generally refers to articles that may be placed against or in proximity to the body of the wearer to absorb and/or retain various liquid wastes discharged from the body. The absorbent article may or may not be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present invention.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
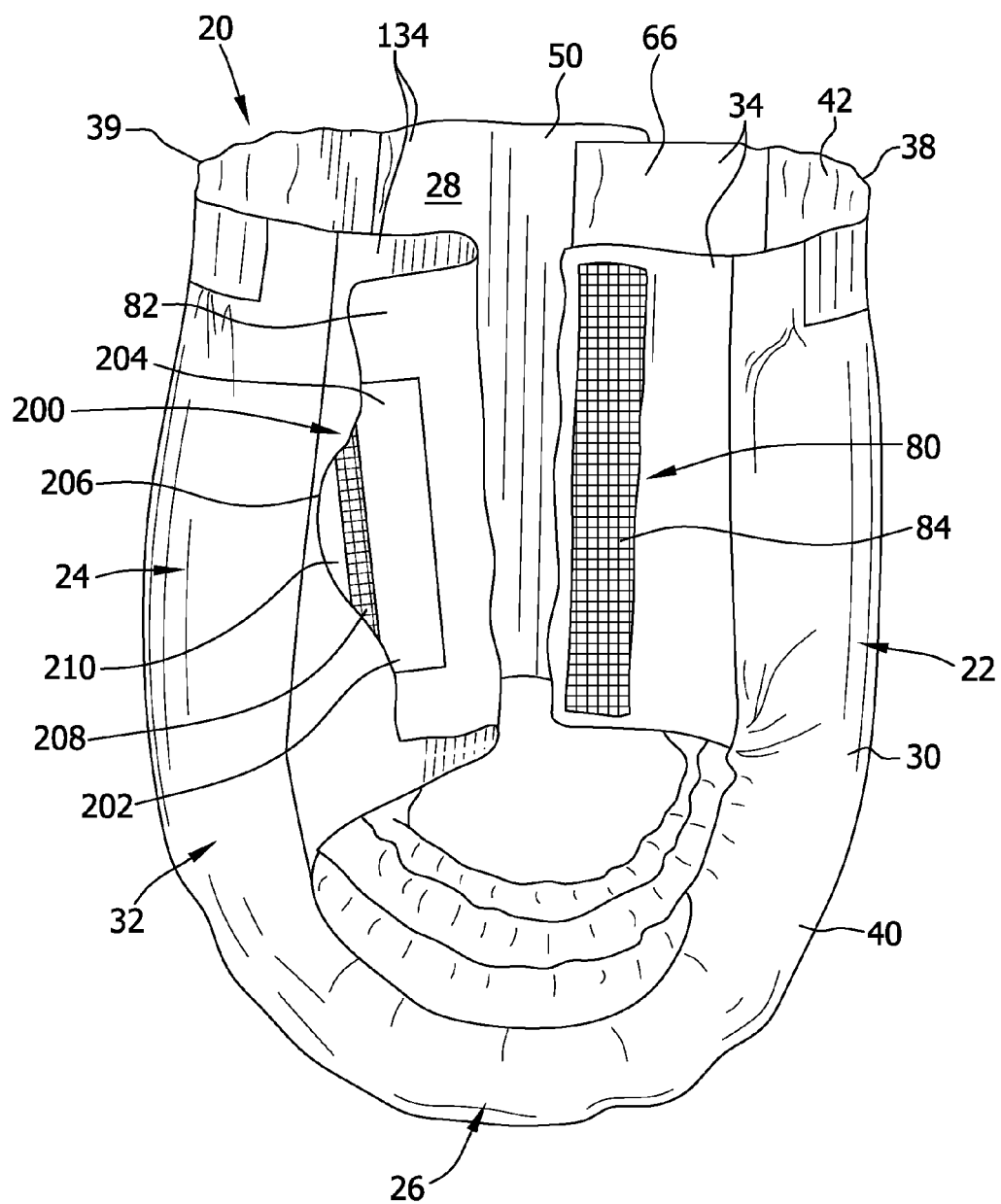
FIG. 2 is a side perspective similar to FIG. 1 with a primary, or article fastening system of the training pants in an unfastened condition on one side of the training pants and the disposal fastening system also in an unfastened condition.

The pair of training pants 20 is illustrated in FIG. 1 in a fully pre-assembled (i.e., as assembled during initial manufacture) configuration (broadly referred to herein as a wear configuration of the pants, i.e., absorbent article) and in FIG. 2 in a partially unfastened condition. The training pants 20 comprises a front waist region 22, a back waist region 24, a crotch region 26 extending longitudinally between and interconnecting the front and back waist regions along a longitudinal direction of the pants, an inner surface 28 configured for contiguous relationship with the wearer, and an outer surface 30 opposite the inner surface. With additional reference to FIGS. 3 and 4, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 3:
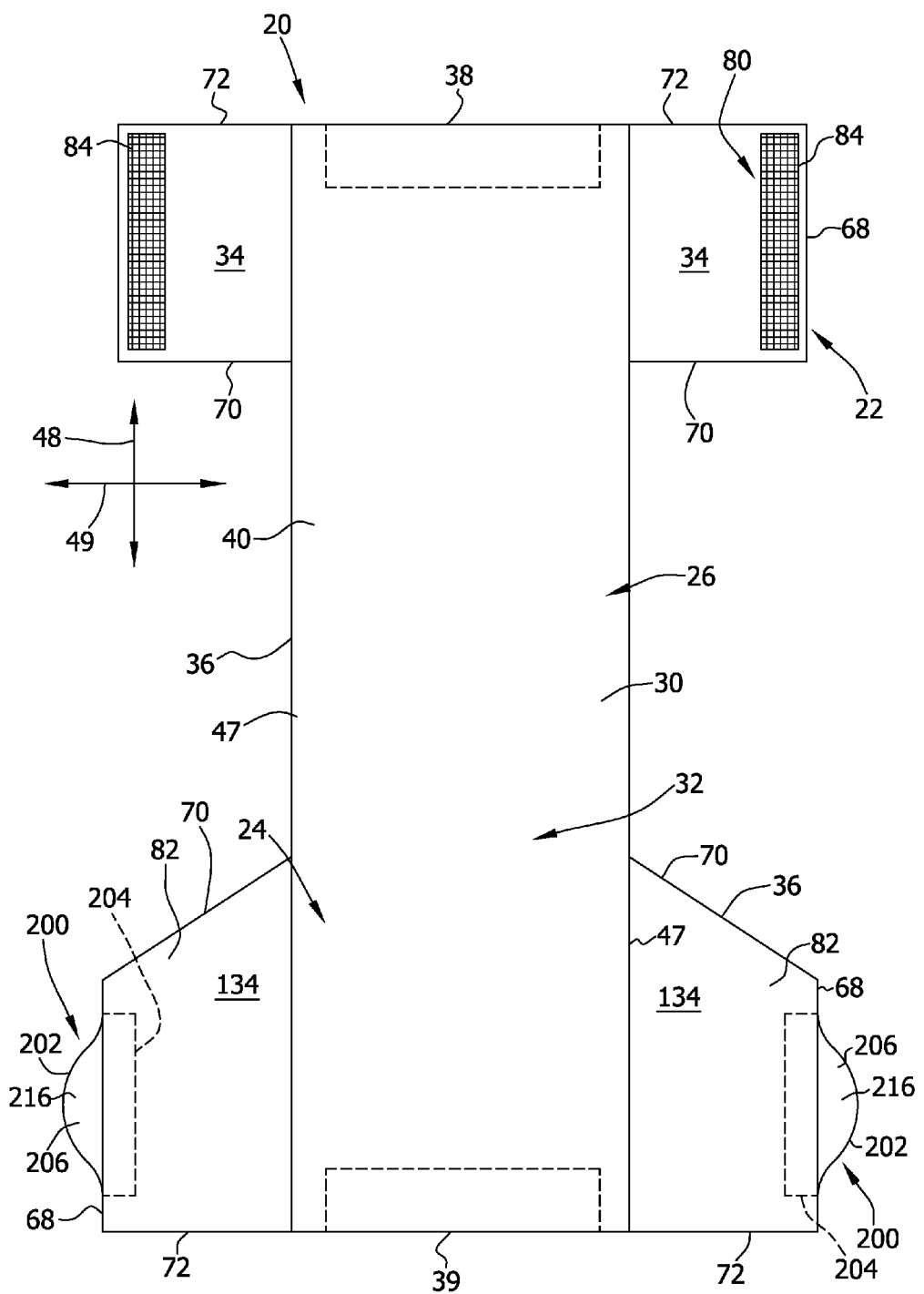
FIG. 3 is a bottom plan view of the training pants of FIG. 1 in an unfastened, unfolded and laid flat condition, and showing the surface of the training pants that faces away from the wearer.
Figure 4:
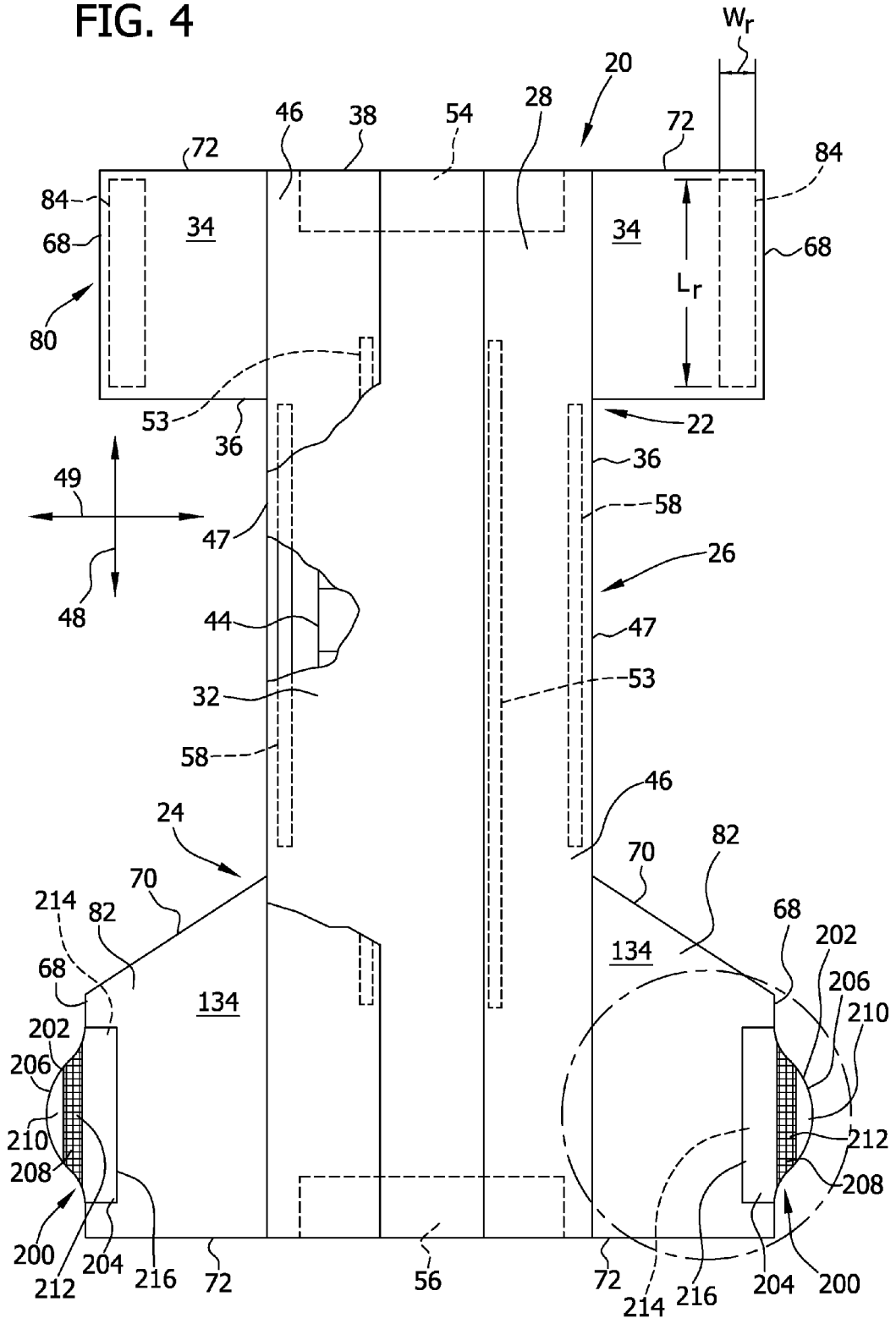
FIG. 4 is a top plan view similar to FIG. 3 showing the surface of the training pants that faces the wearer when worn and with portions cut away to show underlying features.

The illustrated pants 20 comprises a central absorbent assembly, generally indicated at 32, which when laid flat as in FIGS. 3 and 4 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pants). Laterally opposite back side panels 134 extend outward from the absorbent assembly 32 at the back waist region 24 (thereby forming transversely outer portions of the back waist region, and together with the front side panels 34 further defining the sides of the pants).

The central absorbent assembly 32 of the illustrated embodiment comprises an outer cover 40 and a bodyside liner 42 (FIGS. 1 and 2) connected to the outer cover in a superposed relation by suitable means such as adhesives, ultrasonic bonds, thermal bonds or other conventional techniques. An absorbent structure 44 (FIG. 4) is disposed between the outer cover and the bodyside liner. A pair of containment flaps 46 (FIG. 4) is secured to the bodyside liner 42 for inhibiting the lateral flow of body exudates. The central absorbent assembly 32 has opposite ends which form portions of the front and back waist edges 38 and 39, and opposite side edges 47 which form portions of the side edges 36 of the training pants 20 (FIGS. 3 and 4).

Figure 9:
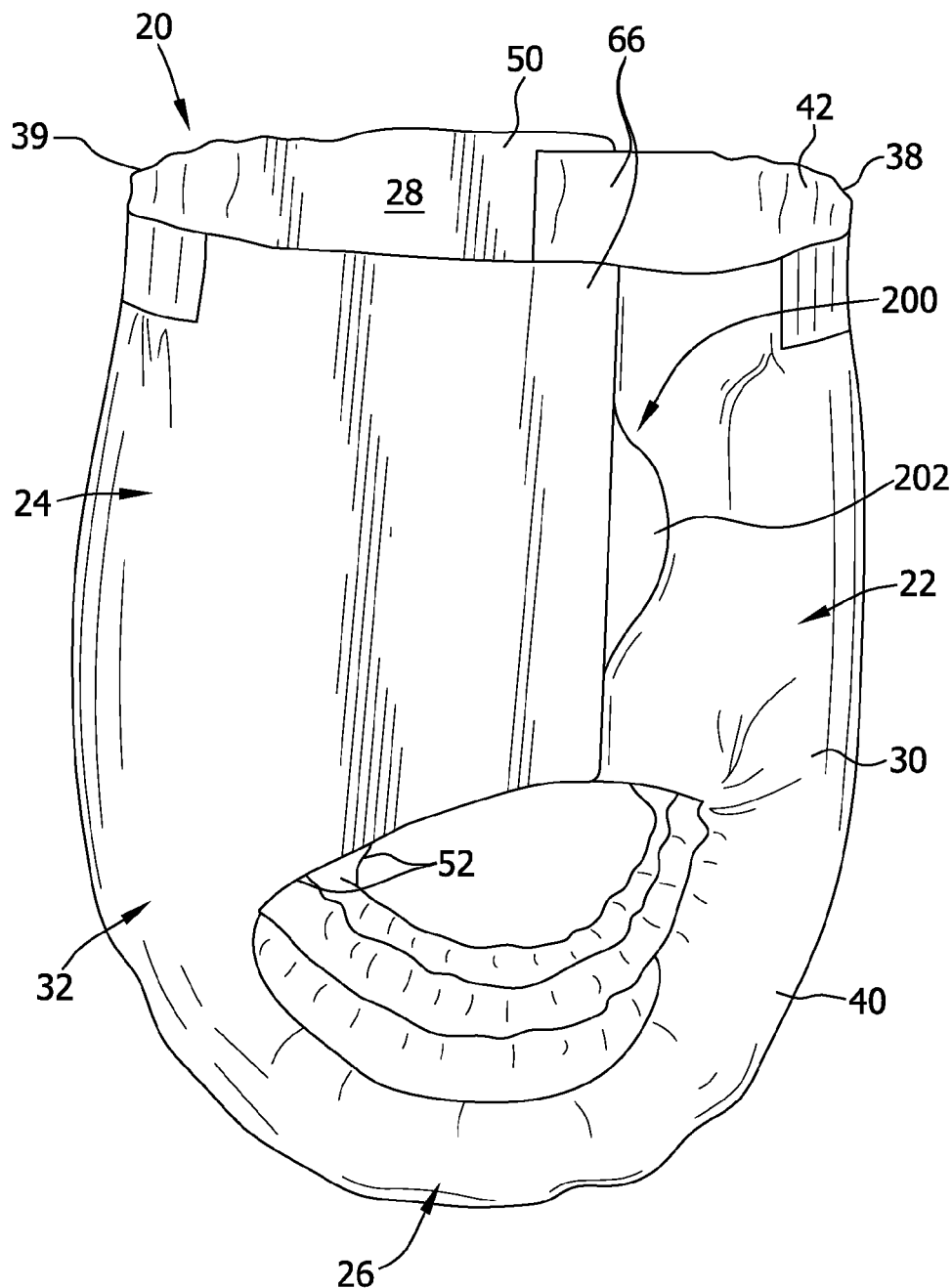
FIG. 9 is a side perspective of a fourth embodiment of a personal wear article in the form of a pair of training pants having a secondary or disposal fastening system illustrated in a fastened condition thereof.

The absorbent assembly 32 and side panels 34, 134 may comprise two or more separate elements, as shown in FIGS. 1 and 2, or they may be integrally formed, as shown in FIG. 9. Integrally formed side panels 34, 134 and absorbent assembly 32 would comprise at least some common materials, such as the bodyside liner, flap composite, outer cover, other materials and/or combinations thereof, and could define a one-piece elastic, stretchable, or nonstretchable pants 20. For further reference, arrows 48 and 49 in FIGS. 3 and 4 depict the orientation of a longitudinal axis and a transverse or lateral axis, respectively, of the training pants 20.

With the training pants 20 in the fastened condition as illustrated fully in FIG. 1 and partially in FIG. 2, the front and back side panels 34, 134 are attached to each other by a primary, or article fastening system 80 to define the pre-assembled three-dimensional wear configuration of the pants, having a waist opening 50 and a pair of leg openings 52. The front waist region 22 comprises the portion of the training pants 20 which, when worn, is positioned at least in part on the front of the wearer while the back waist region 24 comprises the portion of the training pants which is positioned at least in part on the back of the wearer. The crotch region 26 of the training pants 20 comprises the portion of the training pants 20 which is positioned between the legs of the wearer and covers the lower torso of the wearer.

The front and back side panels 34 and 134 comprise the portions of the training pants 20 (and more particularly of the front and back waist regions 22, 24) which, when worn, are positioned on the hips of the wearer. The attached side panels 34, 134 thus broadly define the transversely opposite sides of the pants 20, with each side extending a length Lp (FIG. 5) from the waist opening 50 to the respective leg opening 52 at an engagement seam 66 along which the fastening system 80 releasably attaches the front and back side panels. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 4) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or may only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 4), a rear waist elastic member 56, and leg elastic members 58, as are known to those skilled in the art. The waist elastic members 54 and 56 can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular embodiment, for example, the leg elastic members 58 comprise a plurality of dry-spun coalesced multifilament spandex elastomeric threads sold under the trade name LYCRA and available from E.I. Du Pont de Nemours and Company, Wilmington, Del., U.S.A.

The outer cover 40 suitably comprises a material which is substantially liquid impermeable. The outer cover 40 can be a single layer of liquid impermeable material, but more suitably comprises a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and is desirably one that provides a generally cloth-like texture. The outer layer may also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 may be stretchable, and more suitably elastic. In particular, the outer cover 40 is suitably stretchable and more suitably elastic in at least the transverse, or circumferential direction of the pants 20. In other embodiments the outer cover may be stretchable, and more suitably elastic, in both the transverse and the longitudinal direction.

The liquid permeable bodyside liner 42 is illustrated as overlying the outer cover 40 and absorbent core 44, and may but need not have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 may also be stretchable, and more suitably elastic. In particular, the bodyside liner 42 is suitably stretchable and more suitably elastic in at least the transverse 49, or circumferential direction of the pants 20. In other embodiments the bodyside liner 42 may be stretchable, and more suitably elastic, in both the transverse 49 and the longitudinal 48 directions.

As noted previously, the illustrated training pants 20 have front and back side panels 34 and 134 defining transversely opposite sides of the pants in the wear configuration of the pants. The side panels 34, 134 can be permanently attached along seams 66 to the central absorbent assembly 32 in the respective front and back waist regions 22 and 24. More particularly, as seen best in FIGS. 2 and 3, the front side panels 34 can be permanently attached to and extend transversely outward beyond the side edges 47 of the absorbent assembly 32 in the front waist region 22, and the back side panels 134 can be permanently attached to and extend transversely outward beyond the side edges of the absorbent assembly in the back waist region 24. The side panels 34 and 134 may be attached to the absorbent assembly 32 using attachment means known to those skilled in the art such as adhesive, thermal, pressure or ultrasonic bonding. Alternatively, the side panels 34 and 134 can be formed as an integral portion of a component of the absorbent assembly 32. For example, the side panels can comprise a generally wider portion of the outer cover 40, the bodyside liner 42, and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated embodiment are suitably curved and/or angled relative to the transverse axis 49 to provide a better fit around the wearer's legs. However, it is understood that only one of the leg end edges 70 may be curved or angled, such as the leg end edge of the back waist region 24, or neither of the leg end edges may be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, comprise a stretchable material capable of stretching in a direction generally parallel to the transverse axis 49 of the training pants 20. More suitably the side panels 34, 134 comprise an elastic material. Suitable elastic materials, as well as one process of incorporating stretchable side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the stretch material may comprise a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

In one particularly suitable embodiment at least the front side panels 34 and more suitably both the front and back side panels 34, 134 comprise a vertical filament laminate (VFL) material. A VFL is a composite material having at least one gatherable layer such as a non-woven material and at least one elastic layer. The layers are joined together when the elastic layer is extended from its original condition so that upon relaxing the layers, the gatherable layer is gathered. The composite may be stretched to the extent that the non-elastic material gathered between the bond locations allows the elastic material to elongate. One type of vertical filament laminate is disclosed, for example, by U.S. Pat. No. 6,916,750 to Thomas et al., the content of which is incorporated herein by reference in its entirety. More suitably, the front and back side panels comprise a VFL in which two non-woven (gatherable) layers sandwich an elastic layer so that both faces of the VFL are gatherable. The rugosities formed in the gatherable layers of such a VFL material allow the VFL material to be used as a loop component of a fastening system.

Alternatively, the side panel material may comprise other woven or nonwoven materials, such as those described above as being suitable for the outer cover 40 or bodyside liner 42; mechanically pre-strained composites; or stretchable but inelastic materials.

The absorbent structure 44 can be any structure which is generally compressible, conformable, non-irritating to the wearer's skin and capable of absorbing and retaining liquid body exudates, and may be manufactured in a wide variety of sizes and shapes, and from a wide variety of absorbent materials commonly used in the art. For example, the absorbent structure 44 suitably comprises a matrix of absorbent fibers, and more particularly hydrophilic fibers, such as a web of cellulosic fluff. In a particularly suitable embodiment, the absorbent structure 44 comprises a matrix of cellulosic fluff, such as wood pulp fluff, and superabsorbent particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 44 to better contain and absorb body exudates. The concentration of the superabsorbent particles can also vary through the thickness of the absorbent core 44. Alternatively, the absorbent structure 44 can comprise a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

In one embodiment, the absorbent structure 44 comprises a blend of wood pulp fluff and superabsorbent material. As a general rule, the superabsorbent material is present in the absorbent structure 44 in an amount of from 0 to about 90 weight percent based on total weight of the absorbent assembly. The absorbent structure 44 suitably has a density within the range of about 0.10 to about 0.35 grams per cubic centimeter. The absorbent structure 44 may or may not be wrapped or encompassed by a suitable tissue wrap that may help maintain the integrity and/or shape of the absorbent assembly.

The article fastening system 80 comprises laterally opposite first fastening components 82 adapted for refastenable engagement to corresponding second fastening components 84. In one embodiment, a front or outer surface of each of the fastening components 82, 84 comprises a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 can comprise any refastenable fasteners suitable for absorbent articles, such as adhesive fasteners, cohesive fasteners, mechanical fasteners, or the like. In particular embodiments the fastening components 82, 84 comprise mechanical fastening components for improved performance. Suitable mechanical fastening components can be provided by interlocking geometric shaped materials, such as hooks, loops, bulbs, mushrooms, arrowheads, balls on stems, male and female mating components, buckles, snaps, or the like.

In the illustrated embodiment, the first fastening components 82 (i.e., one on each side of the training pants 20) comprise loop fasteners and the second fastening components 84 comprise complementary hook fasteners. Alternatively, the first fastening components 82 may comprise hook fasteners and the second fastening components 84 may comprise complementary loop fasteners. In another embodiment, the fastening components 82, 84 can comprise interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops may be selected to obtain the desired level of engagement between the fastening components 82, 84. A more aggressive hook material may comprise a material with a greater average hook height and/or a greater percentage of directionally-aligned hooks. When engaged, the fastening components 82, 84 of the illustrated embodiment define the refastenable engagement seams 66 (FIG. 2).

As discussed above, in one particularly suitable embodiment, as best seen in FIGS. 2 and 4, the back side panels 134 are constructed so that the inner surfaces of the respective back side panels define loop fastening components 82 (i.e., the back side panels 134 and fastening components 82 are formed integrally). It is understood, however, that the loop fastening components 82 may be formed separate from the back side panels 134 and attached thereto, such as by adhesive, thermal bonds, ultrasonic bonds, pressure bonds or other suitable techniques without departing from the scope of this invention.

With particular reference now to FIGS. 1 and 2, a secondary, or disposal fastening system, generally indicated at 200, is provided for use in inhibiting pop-opens during wear and for securing the training pants 20 in a compact disposal configuration (FIG. 8B) described in further detail later herein. As illustrated in FIGS. 2 and 4, the disposal fastening system comprises a tab 202 attached to each of the back side panels 134 (broadly, to the transversely opposite sides of the training pants 20) and extending in part transversely outward of the respective back side panels for opposed relationship with the corresponding front side panels in the wear configuration of the pants. As seen best in FIG. 5, each tab 202 comprises an attachment region 204 at which the tab is attached to the respective back side panel 134, and a tab region 206 extending transversely outward from the attachment region. More suitably, the tab region 206 of the tab 202 comprises at least one fastener region 208 having a fastening component 212 for use in securing the pants in their compact disposal configuration, and may further comprise a grip region 210 transversely outward of the fastener region for use in manually gripping and manipulating the tab relative to the pants 20.

The fastening component 212 of the illustrated fastener region 208 comprises a hook fastener. The outer surface of each front side panel 34 suitably defines a corresponding fastening component, e.g., a loop fastener, to permit the tab 202 on each side of the pants 20 to be attached at its fastener region to the respective front side panel (i.e., broadly, to the pants) in the wear configuration of the pants. For example, the front side panel 34 in one particularly suitable embodiment may be constructed of VFL material as described previously so that the outer surface of the front side panel itself defines a loop fastening component. Alternatively, a loop fastener component (not shown) may be formed separate from the front side panel 34 and attached to the panel outer surface without departing from the scope of this invention. The outer facing surface 30 of the outer cover 40 of the pants 20 is also suitably constructed to define a loop fastener, such as by forming the outer cover of a material that defines a loop fastening component (e.g., VFL or other suitable material) or by forming a separate loop fastening component and attaching it to the outer surface of the pants outer cover, to permit attachment of the tab 202 to the outer cover in the disposal configuration of the pants.

It is understood that the fastening component(s) 212 defining the one or more fastener regions 208 of the tab 202 may instead be a loop fastener component, with the outer surfaces of the front side panels 34 and outer cover 40 of the pants 20 being constructed to define corresponding hook fastening components. In other embodiments, the fastening component 212 defining the tab fastener region(s) 208 and the outer surfaces of the front side panels 34 and pants outer cover 40 may comprise other suitable releasably attachable fasteners without departing from the scope of this invention. It is also contemplated that the fastening component 212 defining the tab fastener region 208 may be releasably attachable to the pants 20 (e.g., to the front side panel 34) in the wear configuration but otherwise more permanently attachable elsewhere on the pants (e.g., to the outer cover 40) in the disposal configuration of the pants. The term permanent attachment is intended herein to refer to an attachment that is generally not releasable without some damage or substantially reduced ability to reattach to the fastening component and/or the component to which the fastening component is attached.

Also, in the illustrated embodiment the tabs 202 attach to the outer surfaces of the front side panels 34 (e.g., outer surface 30 of pants 20) in the wear configuration of the article. But it is contemplated that in the wear configuration the tabs 202 may be configured to attach to the inner surfaces of the front side panels 34 (e.g., inner surface 28 of pants 20) and remain within the scope of this invention.

The attachment region 204 of each tab 202 is suitably attached to the respective back side panel 134 (broadly, to the respective side of the pants 20) and in the illustrated embodiment is attached to the inner surface of the back side panel. It is understood, however, that the attachment region 204 may instead be attached to the outer surface of the back side panel 134 in a manner similar to that illustrated in the alternative embodiment of FIG. 7. The attachment region 204, in the illustrated embodiment in which the back side panel 134 overlaps the front side panel 34, is more suitably attached to the back side panel adjacent the transverse edge of the back side panel. But the attachment region 204 may instead be attached to the back side panel 134 more transversely distal from the transverse edge of the back side panel, such as when the front side panel 34 overlaps the back side panel, without departing from the scope of this invention.

In one embodiment, the sides of the pants, i.e., extending from the waist opening 50 to the respective leg openings 52 (and more particularly, in the illustrated embodiment where the front and back side panels 34, 134 are attached to define the engagement seam 66 therebetween) has a length Lp extending from the waist opening of the pants to the leg opening thereof of at least about 50 mm, more suitably at least about 75 mm, more suitably at least about 90 mm, still more suitably at least about 110 mm and even more suitably at least about 125 mm for a children's training pants. It is understood that for pants-like articles sized for adults, such as adult incontinence garments, the length Lp of the sides of the pants, such as at the engagement seam 66 between the front and back side panels 34, 134, may be greater than as set forth above, such as up to about 300 mm or more and remain within the scope of this invention.

The attachment region 204 of each tab 202 suitably has a greatest length La (FIG. 5) in the range of about 35 percent to 100 percent of the length Lp of the side of the pants 20 at the engagement seam 66, and more suitably in the range of about 45 percent to 100 percent thereof. Even more suitably, the greatest length La of the tab attachment region 204 is at least about 50 percent of the length Lp of the side of the pants 20 at the engagement seam 66, such as in the range of about 50 percent to 100 percent, and still more suitably the greatest length La is about 60 percent of the length Lp of the side of the pants at the engagement seam. In one particular embodiment, the greatest length La of the tab attachment region 204 is 100 percent of the length Lp of the side of the pants 20 at the engagement seam. The term greatest length (or width) as used herein in reference to various component dimensions is intended to refer to a greatest extent or reach of a component along a prescribed direction, recognizing that the various components herein may not be of a uniform (e.g., square or rectangular) shape, and is not intended to define any design limitations or upper limits on the size and shape of the component. It is understood, for example, that the attachment region 204 of the tab 202 need not be of uniform length to remain within the scope of this invention.

The attachment region 204 of each tab 202 is suitably attached to the inner surface of the back side panel 134, such as by adhesive, thermal bonding, ultrasonic bonding, pressure bonding or other suitable attachment technique. More suitably, an attachment face 214 (FIG. 4) of each tab 202 is attached to the inner surface of the back side panel 134 at the attachment region 204 of the tab. The tab region 206 of each tab 202 extends transversely outward of the attachment region 204 into overlapping or opposed relationship with the outer surface of the corresponding front side panel 34 so that the tab region is accessible exterior of the pants 20 in the wear configuration of the pants. It is understood, however, that the tab region 206 may instead be in opposed relationship with and releasably attachable to the inner surface of the front side panel 34 without departing from the scope of this invention.

In one exemplary embodiment, the engagement seam 66 along which the front and back side panels 34, 134 (and more broadly, the front and back waist regions 22, 24) are releasably attached by the article fastening system 80 has a greatest length Lr (FIG. 2, which in the illustrated embodiment is defined by the greatest length of the hook fastening component 84 of the fastening system 80). The length Lr of the engagement seam 66 may be equal to the length Lp of the side of the pants 20 (i.e., extending from the waist opening 50 to the leg opening 52), slightly less than the length Lp of the side of the pants as in the illustrated embodiment, or considerably less than the length Lp of the side of the pants.

Each tab 202 and more particularly the attachment region 204 thereof is suitably sized in length relative to the length Lr of the engagement seam 66 so that the greatest length La of the attachment region of the tab is in the range of about 35 to about 95 percent of the greatest length Lr of the engagement seam and more suitably about 50 to about 80 percent. It is understood, however, that the greatest length La of the attachment region 204 may be other than as set forth above without departing from the scope of this invention. For example, in particular embodiments, the greatest length La of the attachment region can be equal to, or even greater than, the greatest length Lr of the engagement seam.

Additionally, the engagement seam 66 along which the front and back side panels 34, 134 are releasably attached by the article fastening system 80 has a greatest width Wr (FIG. 4), which in the illustrated embodiment is defined by the greatest width of the hook fastening component 84 of the fastening system 80. The attachment region 204 has a greatest width Wa which can be equal to, less than, or greater than the greatest width Wr of the engagement seam 66. Similarly, the attachment region 204 has a greatest width Wa which can be equal to, less than, or greater than the greatest width of the fastening component 84.

The tab region 206 of each tab 202, i.e., the portion of the tab that extends transversely outward from the attachment region 204 (and in the illustrated embodiment comprises the fastener region 208 and grip region 210 of the tab), suitably extends transversely outward from the attachment region a greatest distance Dt of about 5 mm to about 20 mm. The tab region 206 of each tab 202 illustrated in FIGS. 1-4 is generally rounded and has a single peak defining the greatest transverse distance Dt of the tab region outward from the attachment region 204 of the tab. It is understood, however, that the tab region 206 may be shaped other than as illustrated without departing from the scope of this invention. For example, in the alternative embodiments of FIGS. 6 and 7 a tab 502, 702 (respectively) is illustrated as having a dual peak configuration with each peak defining the greatest distance Dt of the tab region outward from the attachment region.

In another embodiment the greatest distance Dt that the tab region 206 extends transversely outward from the attachment region 204 is in the range of about 5 to about 30 percent of the greatest length La of the attachment region of the tab 202, and more suitably in the range of about 10 to about 20 percent thereof.

In the various embodiments herein, the tab region 206 of each tab 202 is suitably positioned generally centrally along the length Lp of the side of the pants 20 (e.g., between the waist opening 50 and respective leg opening 52), and in particular at the engagement seam 66 between the front and back side panels 34, 134. More suitably, the tab region 206 has a transversely extending centerline C and this centerline is disposed within about 20 percent of the midpoint along the length Lp of the side of the pants 20, and in particular at the engagement seam 66, and even more suitably within about 10 percent of the length Lp at the engagement seam 66.

The tab region 206 also has a greatest length Lt, such as where the tab region attaches to (or in the illustrated embodiment is integral with) the attachment region 204 of the tab 202. This greatest length Lt of the tab region 206 is suitably in the range of about 10 to about 70 percent of the length Lp of the side of the pants 20, and in particular at the engagement seam 66, and more suitably in the range of about 25 to about 45 percent. While in the illustrated embodiment the greatest length Lt of the tab region 206 is less than the greatest length La of the attachment region 204, it is contemplated that the tab region greatest length Lt may be substantially equal to and may even be greater than the greatest length La of the tab attachment region 204.

Figure 5:
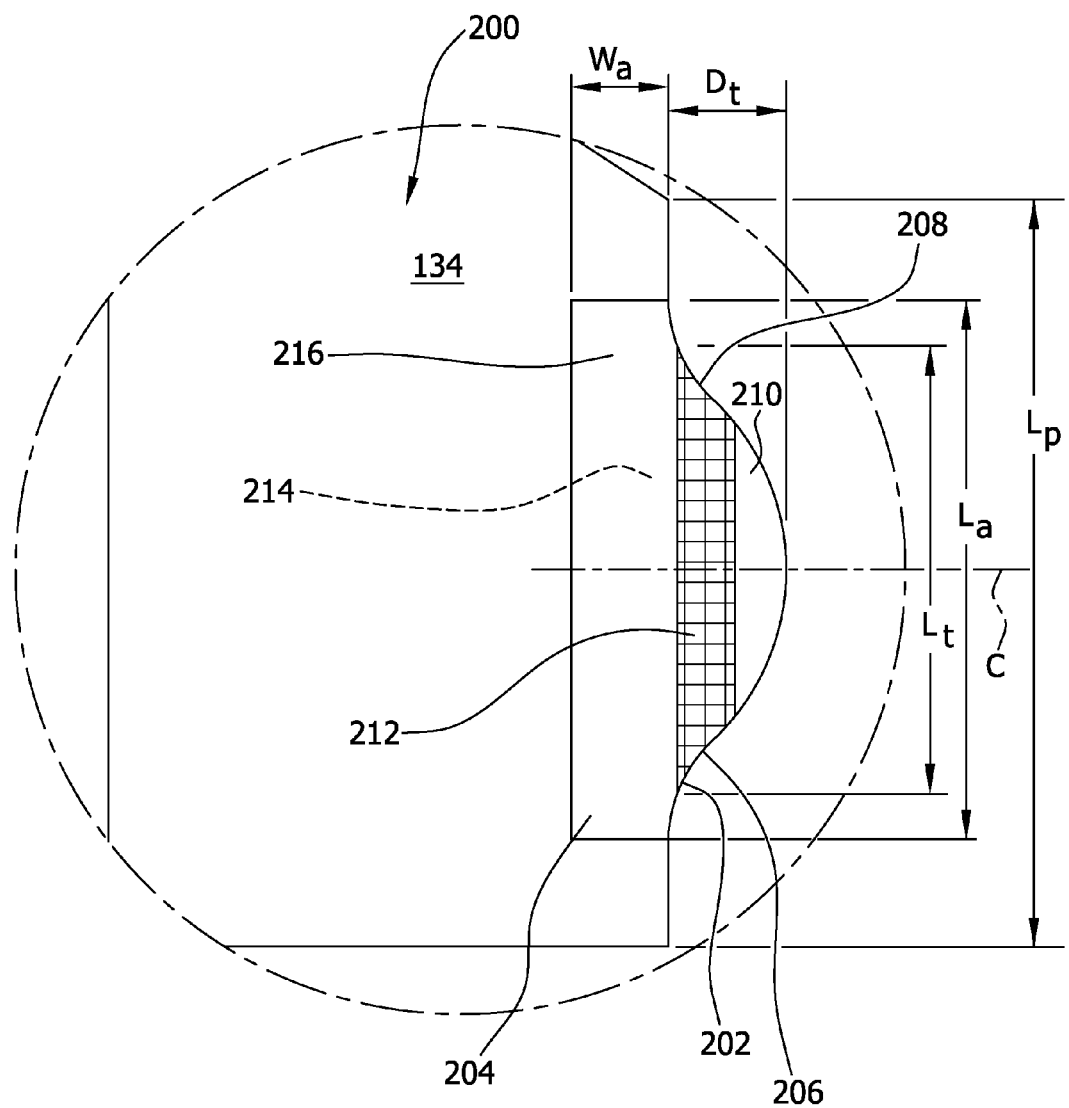
FIG. 5 is a an enlarged fragmented view of the encircled area of FIG. 4.

With reference to FIG. 5, the fastener region 208 of each tab 202 suitably extends lengthwise of the tab, within the tab region 206 thereof, to the edges of the tab at the tab region. It is understood, however, that the fastener region 208 need not extend the full length of the tab 202 at the tab region 206 to remain within the scope of this invention.

When the tab 202 includes a grip region 210, such as in the illustrated embodiment of FIGS. 1-4, the tab is suitably constructed so that the grip region is non-attachable to the pants (i.e., the absorbent article) at least in the wear configuration of the pants. The term non-attachable as used in this instance means that the grip region 210 is not releasably or otherwise removably attachable to the pants in the wear configuration thereof, nor is the grip region permanently attached to the pants. In one embodiment, the grip region 210 extends transversely outward from the fastener region 208 of each tab 202 a distance of at least about 1 mm, such as in the range of about 1 mm to about 10 mm to provide sufficient unattached material of the tab for readily gripping and pulling on the tab.

In one embodiment, each tab 202 is suitably constructed of a base substrate 216 having a fastening component 212 (e.g., a hook fastening component in the illustrated embodiment) attached thereto such as by adhesive bonding, thermal bonding, ultrasonic bonding, pressure bonding or other suitable technique to define the fastener region 208 of the tab. In certain embodiments, the base substrate 216 may be constructed such that, other than the fastener region 208, the tab is not releasably attachable to the pants 20, particularly at the grip region 210 (if provided) of the tab. In one particularly suitable embodiment, the base substrate 216 is less stretchable (at least in the transverse direction thereof) than the pants 20 (in the transverse, or circumferential direction thereof) and more suitably the base substrate is non-stretchable so that pulling on the tab transversely of pants 20 to secure the pants in their disposal configuration, the pants (and in particular the back side panels 134) are allowed to stretch. As an example, one suitable material from which the base substrate 216 may be constructed is a three-layer nonwoven polypropylene material known as SMS. SMS is an acronym for Spunbond, Meltblown, Spunbond, the process by which the three layers are constructed and then laminated together. One example of an SMS material is described in U.S. Pat. No. 4,041,203 to Brock et al. It should be noted, however, that other nonwovens as well as other materials including wovens, films, foam/film laminates and combinations thereof may be used to construct the tab 202 without departing from the scope of this invention.

In particular embodiments, the base substrate 216 is constructed of a material that is releasably attachable with the fastener component 84 of the primary fastening system 80. For example, in particular embodiments, the base substrate 216 is formed from a material such as acrylic, polyamide, polyethylene, polypropylene or polyester, and is formed into a "loop"-type material by methods such as warp knitting, stitch bonding or needle punching. The base substrate 216 can comprise any fibrous structure capable of entangling or catching hook materials, such as carded, spunbonded or other nonwoven webs or composites, including elastomeric and nonelastomeric composites. One material suitable for use as a base substrate 216 is available from Guilford Mills, Inc., Greensboro, N.C., U.S.A. under the trade designation No. 36549. Another suitable base substrate material comprises a pattern un-bonded web as disclosed in co-assigned U.S. Pat. No. 5,858,515 issued Jan. 12, 1999 to Stokes, et al., which is incorporated herein by reference to the extent consistent herewith. In particular embodiments, the base substrate 216 can include a "loop"-type material as just discussed but that is attached to a backing structure, and the composite is then attached to the article 20, such as along the side edges of the front or back side panels 34, 134.

As previously discussed, in particular embodiments each of the transversely opposite sides of the article comprise a material (such as, for example, a nonwoven material) that is releasably engageable with the hook material of the primary fastening system. When the article is fastened in the wear configuration, it is possible in certain embodiments that the hook material of the primary fastening system simultaneously engages both the disposal-tab base substrate and an outer facing of the transversely opposite sides of the article (such as, for example, the outermost nonwoven facing of an elastomeric nonwoven laminate). For example, if the greatest length La of the attachment region of the tab is less than the greatest length Lr of the engagement seam, it is probable that the refastenable seam 66 will be formed not only by engagement of the hook component 84 to the base substrate 216, but also by engagement of the hook component 84 to portions of the outer facing of the side panel 134 that extend beyond the longitudinal ends of the attachment region 204 of the tab 202, as representatively illustrated in FIG. 1.

Similarly, if the greatest width Wa of the attachment region of the tab is less than the greatest width Wr of the engagement seam, it is probable that the refastenable seam 66 will be formed not only by engagement of the hook component 84 to the base substrate 216, but also by engagement of the hook component 84 to portions of the outer facing of the side panel 134 that extend transversely inward of the longitudinal side edge of the attachment region 204 of the tab 202, as representatively illustrated in FIG. 1. However, it is not necessary that the hook material 84 of the primary fastening system 80 simultaneously engage both the disposal-tab base substrate 216 and the transversely opposite sides of the article. For example, if the greatest length La of the attachment region of the tab is greater than the greatest length Lr of the engagement seam, and/or if the greatest width Wa of the attachment region of the tab is greater than that the greatest width Wr of the engagement seam, the refastenable seam 66 may be formed solely by engagement of the hook component 84 to the base substrate 216.

In one particularly suitable embodiment, at least the tab region 206 of the tab 202 and more suitably the entire tab has a stiffness that is greater than a stiffness of the components of the pants 20 to which the tab is attached, e.g., the side panels 34, 134, the outer cover 40, or the bodyside liner 42. For example, the stiffness of the tab 202 is at least about 10 milligrams greater than the stiffness of the side panels 34, 134, the outer cover 40, and/or the bodyside liner 42. In one suitable embodiment, the tab 202 has a stiffness in the range of about 10 milligrams to about 10,000 milligrams and more suitably between about 10 milligrams and about 2,000 milligrams.

As used herein, stiffness is the resistance of a body to deflection or deformation (e.g., bending) when acted on by an applied force. The stiffness of the tab 202 and the other components of the pants 20 (e.g., the side panels 34, 134, the outer cover 40, and the body side liner 42) can be determined with respect to a bending moment produced by a force that is directed perpendicular to the plane substantially defined by the length and width of the component being tested. One suitable technique for determining the stiffness values described herein is a Gurley Stiffness test, a description of which is set forth in TAPPI Standard Test T 543 om-94 (Bending Resistance of Paper (Gurley type tester)). A suitable testing apparatus is a Gurley Digital Stiffness Tester; Model 4171-D manufactured by Teledyne Gurley, a business having offices in Troy, N.Y. For purposes of the present description, the stated stiffness values are intended to correspond to the values that would be generated by a "standard" sized sample using the Gurley stiffness tester. Accordingly, the scale readings from the Gurley stiffness tester are appropriately converted to the stiffness of a standard size sample, and are traditionally reported in terms of milligrams of force (mgf). Currently, a standard "Gurley unit" is equal to a stiffness value of 1 mgf, and may equivalently be employed to report the Gurley stiffness.

As a result of the increased stiffness as compared to the other components of the pants 20 (e.g., the side panels 34, 134, the outer cover 40, and the body side liner 42), the tab 202 and specifically the grip region 210 thereof provides an area that is easy for a user to grasp. Thus, the tab 202 facilitates easy manipulation of the pants 20 between its various configurations. A user of the pants 20 can disengage the fastener region 208 of the tab 202 from the front side panel 34 using one-hand. The user can grasp the relatively stiff grip region 210 of the tab 202 between their thumb and forefinger and pull tab 202 including the fastener region 208 away from the front side panel 34 to thereby disengage the tab from the front side panel.

In addition, the greater stiffness of the tab 202 results in increased attachment between the fastening region 208 of the tab and the respective front side panel 34 as compared to the engagement seams 66, which are formed between components having a lower stiffness. The increased stiffness of the tab 202 inhibits bending, folding, etc. of at least the fastener region 208 thereof relative to the front side panel 34 to which it is attached thereby reducing the potential for pop-opens.

When the pants 20 are donned by the wearer, the tabs 202 are disposed near the hips or slightly inward of the hips of the wearer so that the relatively stiff tabs do not compromise the comfort of the pants. That is, the tabs 202 are located such that the wearer can freely bend and otherwise move without any significant impediment by the tabs.

The thickness and the basis weight of the base substrate 216 may generally vary. For example, the basis weight of the base substrate 216 may be in the range of about 20 grams per square meter ("gsm") to about 160 gsm and, in some embodiments, from about 20 gsm to about 80 gsm. In one particularly suitable embodiment, the basis weight of the base substrate 216 is about 60 gsm. The thickness of the base substrate 216 may suitable be in the range of about 0.165 inches (4.2 millimeters (mm)) to about 0.190 inches (4.8 mm), in some embodiments from about 0.170 inches (4.3 mm) to about 0.185 inches (4.7 mm), and in other embodiments, from about 0.175 inches (4.45 mm) to about 0.180 inches (4.6 mm). The thickness can be measured on an Ames model 482 Comparator using an Ames model 130 base with an auxiliary weight to provide 0.25 psi.

In use, the training pants 20 are constructed and pre-assembled in their wear configuration, with the article fastening system 80 releasably attaching the front and back waist regions 22, 24 (and more particularly the front and back side panels 34, 134 in the illustrated embodiment). The fastener region 208 of each tab 202 is releasably attached to the outer surface of the respective front side panel 34 to releasably attach the tab region 206 of each tab to the pants 20 in the wear configuration of the pants.

When the pants 20 are to be discarded after use, the pants may be slipped off of the wearer in the manner of conventional underpants, or the front and back waist regions 22, 24 may be detached from each other (e.g., by separation of the fastening components 82, 84 of the article fastening system 80) and the pants removed from the wearer. Where the front and back waist regions 22, 24 are separated to remove the pants, the fastener regions 208 of the tabs 202 must be detached from the front waist region (e.g., from the front side panels 34). To detach the fastener regions 208 of the tabs 202 illustrated in the embodiment of FIGS. 1-4, the grip region 210 of each tab is gripped between the thumb and forefinger and pulled away from the front side panel 34 until the fastener region breaks free from its attachment to the front side panel. The relatively stiff tab 202 provides an area of the pants 20 that is easy for the user to grasp and manipulate the pants to break the attachment between the fastener component 212 of the tab and the front side panel 34.

Figure 8A:
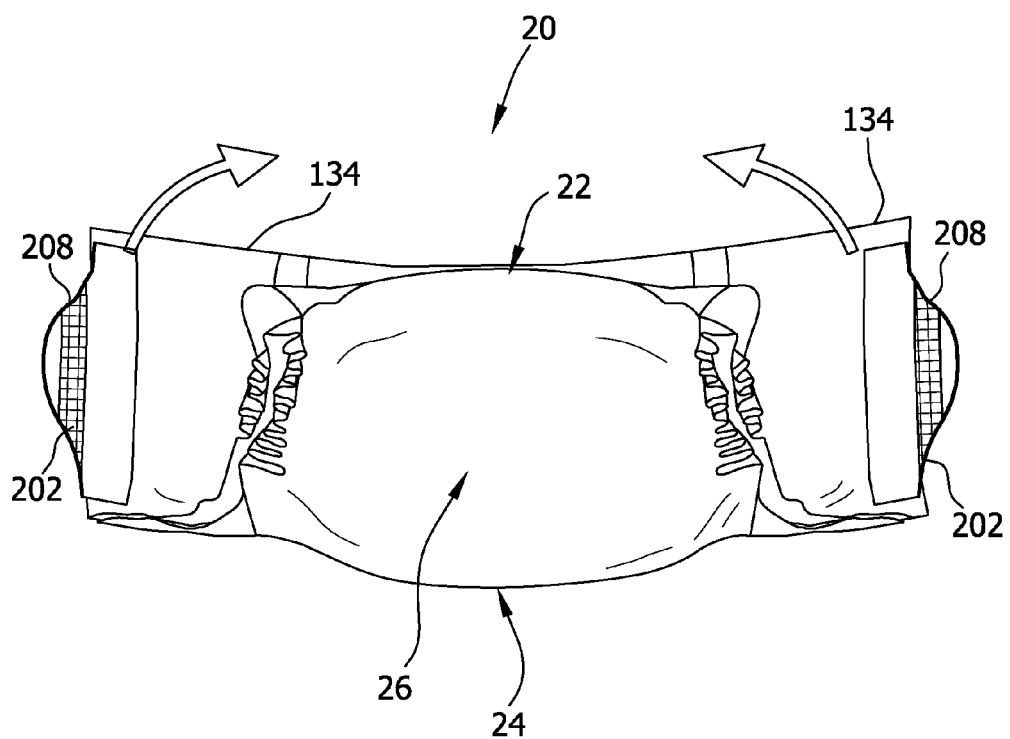
FIG. 8A is a schematic of the training pants of FIG. 1 in a partially compacted discard configuration.

To dispose of the used pants 20, the pants are laid on a surface with the back waist region 24 down against the surface and with the front and back waist regions 22, 24 in opposed relationship with each other. The sides, and more particularly the front and back side panels 34, 134 in the illustrated embodiment, suitably extend transversely outward in opposed relationship with each other. With reference to FIG. 8A, the crotch region 26 and a portion of the back waist region 24 of the pants 20 are then folded or rolled up over the front waist region 22 of the pants. If not already done, the tab regions 206 of the tabs 202 are gripped at the grip regions 210 thereof and are pulled away from the pants 20 to detach the tabs from the pants (i.e., from the front side panels 34 in the illustrated embodiment). While gripping the detached tab regions 206 of the tabs 202, the tabs are pulled around the folded or rolled portion of the pants 20 and then toward each other as indicated by the direction arrows in FIG. 8A.

Figure 8B:
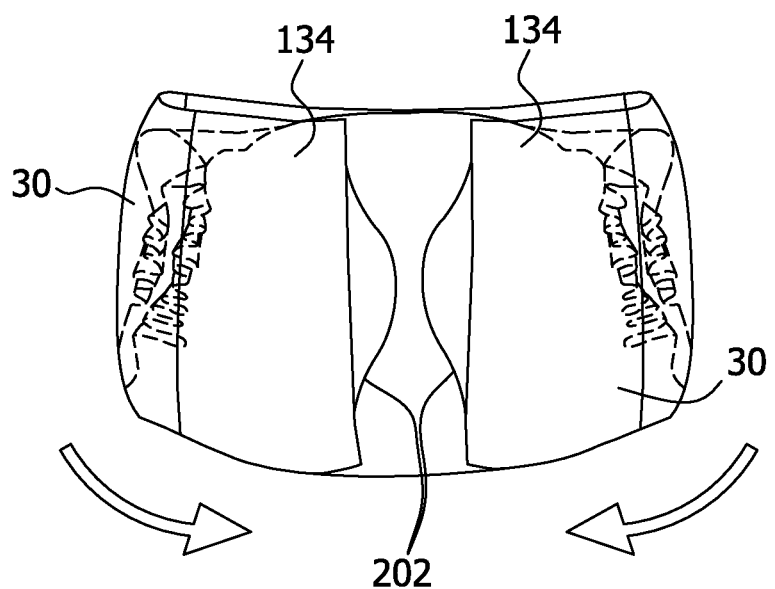
FIG. 8B is a schematic of the training pants of FIG. 8A in a fully compacted discard configuration with the disposal fastening system in a fastened condition to secure the pants in the discard configuration.

Pulling on the tabs 202 in this manner pulls on and suitably stretches the stretchable back waist region 24 (and more particularly the stretchable back side panels 134 in the illustrated embodiment) so that the back waist region and more suitably the back side panels substantially surround the folded or rolled portion of the pants 20. The fastener regions 208 of the tabs 202 are attached to the folded or rolled portion of the pants 20 (i.e., to the outer surface 30 of the pants) to thereby secure the pants in their compact disposal configuration as illustrated in FIG. 8B. Pulling on and stretching the back waist region 24 of the pants 20 to surround the folded or rolled portion also places in tension (e.g., due to the elasticity in the elastic back side panels 134) a substantial transverse or circumferential segment of the circumscribing portion of the pants (e.g., the back waist region and more particularly the back side panels in the illustrated embodiment) in the disposal configuration of the pants. This allows the pants 20 to be relatively compact in the disposal configuration and to be held generally tightly in this compact configuration to reduce the risk of leakage from the pants.

While in FIG. 8B the tabs 202 are brought into positions generally adjacent each other to secure the pants 20 in the disposal configuration thereof, it is contemplated that one of the tabs may be pulled across the longitudinal centerline of the pants and secured thereto (e.g., to the outer surface 30 of the pants), and then the other tab pulled across the longitudinal centerline over and beyond the one tab and secured to the pants, such as the back side panel 134 to which the one tab is attached since it is of a VFL material, to provide a further compacted disposal configuration of the pants.

Figure 6:
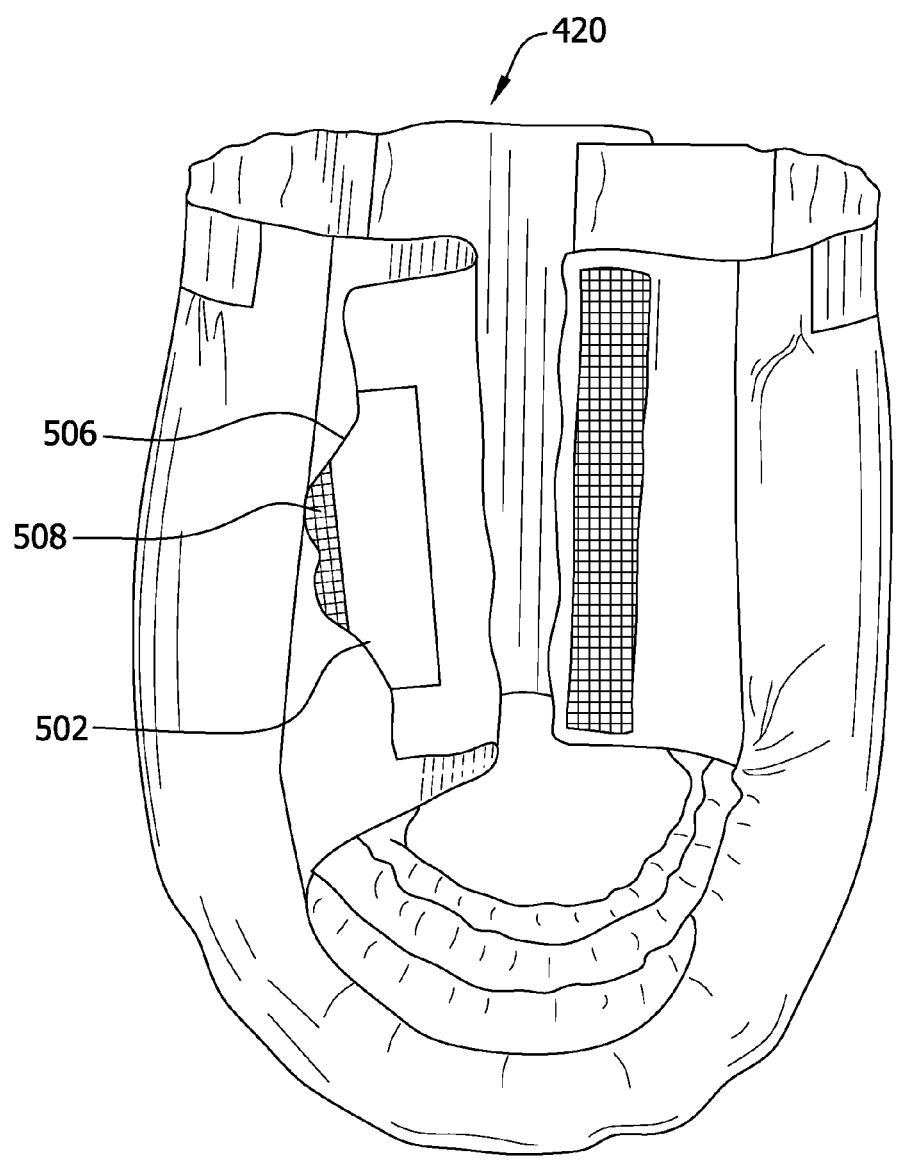
FIG. 6 a side perspective of a second embodiment of a personal wear article in the form of a pair of training pants with a primary, or article fastening system of the training pants in a unfastened condition on one side of the training pants and a secondary, or disposal fastening system also in an unfastened condition on that same side of the training pants.

FIG. 6 illustrates an alternative embodiment of an absorbent article for personal wear, also in the form of a pair of training pants 420, having secondary, or tabs 502 similar to the tabs 202 of the embodiment of FIGS. 1-4 but with a tab region 506 configured to have a double peak arrangement. The fastener region 508 of each tab 502 of this embodiment extends transversely to the end of the tab region 506 so that a grip region is omitted from the tab.

Figure 7:
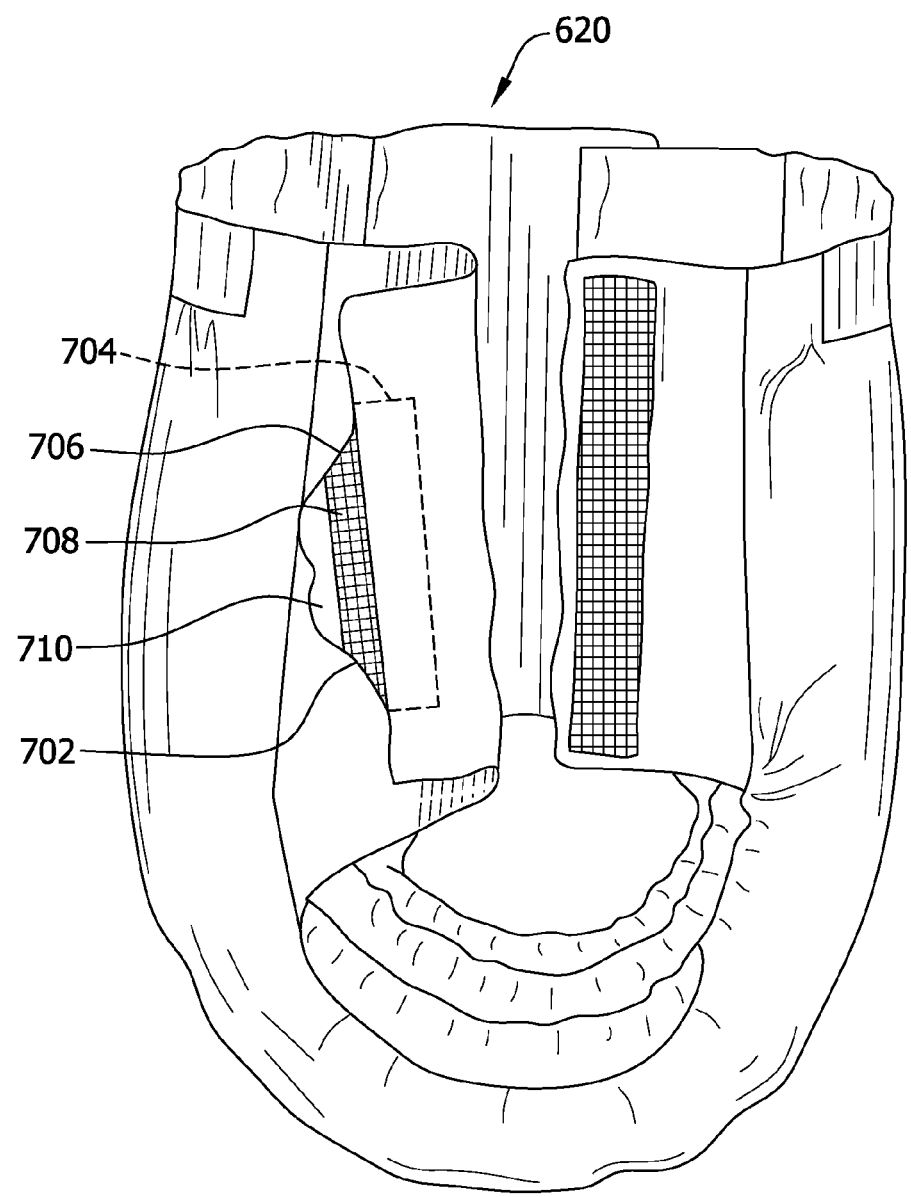
FIG. 7 a side perspective of a third embodiment of a personal wear article in the form of a pair of training pants with a primary, or article fastening system of the training pants in a unfastened condition on one side of the training pants and a secondary, or disposal fastening system also in an unfastened condition on that same side of the training pants.

FIG. 7 illustrates another alternative embodiment of an absorbent article for personal wear, also in the form of a pair of training pants 620, similar to that of FIG. 6 but with the tabs 702 having attachment regions 704 attached to the outer surfaces of the back side panels 734 (broadly, to the outer surface 730 of the back waist region 724) of the pants. The tab region 706 of each tab 702 of this embodiment is configured to have both a fastener region 708 and a grip region 710 transversely outward of the attachment region 704.

Figure 10:
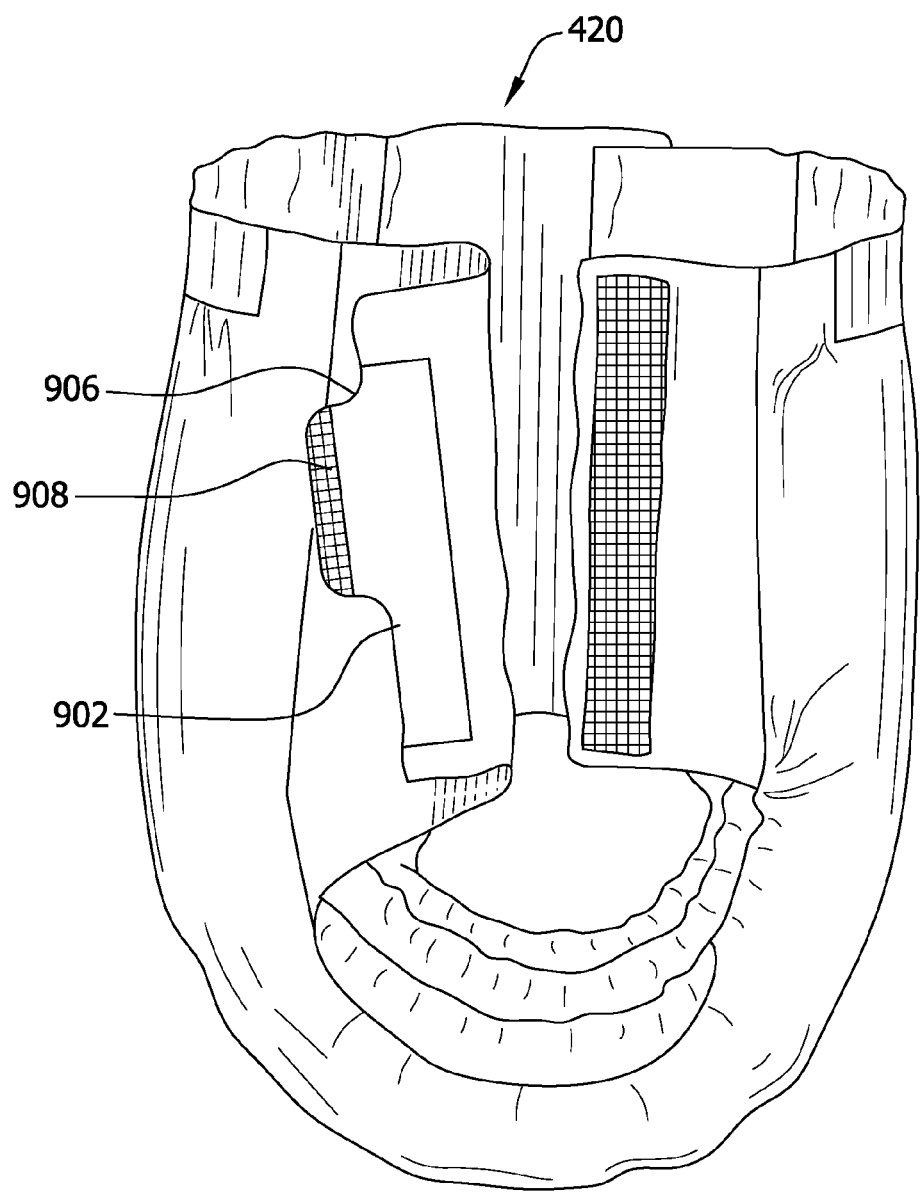
FIG. 10 is a side perspective of a fifth embodiment of a personal wear article in the form of a pair of training pants with a primary, or article fastening system of the training pants in an unfastened condition on one side of the training pants and a secondary, or disposal fastening system also in an unfastened condition on that same side of the training pants.

FIG. 10 illustrates an alternative embodiment of an absorbent article for personal wear, also in the form of a pair of training pants 820, similar to that of FIG. 1 but with the tab regions 906 of the disposal tabs 902 offset from the centerline of the attachment region. In this manner, for example, the tab regions 906 are nearer to the waist opening 50 than to the leg opening of the pants 52.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. An absorbent article for personal wear about a wearer's waist, said article comprising:
    a central absorbent assembly comprising a liquid permeable inner layer for facing the wearer, an outer layer for facing away from the wearer, an absorbent body disposed therebetween, a front waist region, a back waist region and a crotch region extending longitudinally between and interconnecting the front and back waist regions;
    a pair of transversely spaced front side panels extending transversely outward from the front waist region;
    a pair of transversely spaced back side panels extending transversely outward from the back waist region, the back side panels being attached to the front side panels to define a wear configuration of the absorbent article having a waist opening, a pair of leg openings spaced from the waist opening, and transversely opposite sides defined by the front and back side panels and having a length extending from the waist opening to the respective leg opening; and
    a pair of tabs, each tab having an attachment region attached to one of said front side panels and said back side panels, and a tab region extending transversely outward from the attachment region and being releasably attachable to the other one of said front side panels and said back side panels, said one of the front side panels and said back side panels to which the attachment region of the respective tab is attached having a first stiffness, at least a portion of the tab region of the respective tab having a second stiffness greater than said first stiffness, each of the back side panels being directly attached to respective front side panels in the wear configuration of the absorbent article by engagement of fastener components mounted on said other one of said front side panels and said back side panels with the attachment region of the tabs.

2. The absorbent article set forth in claim 1 wherein said second stiffness of said portion of the tab region of the respective tab is at least about 10 milligrams greater than said first stiffness of said one of the front side panels and the back side panels to which the tab attachment region is attached.

3. The absorbent article set forth in claim 1 wherein said second stiffness of said portion of the tab region of the respective tab is in the range of about 10 milligrams to about 10,000 milligrams greater than said first stiffness of said one of the front side panels and the back side panels to which the tab attachment region is attached.

4. The absorbent article set forth in claim 1 wherein the other one of said front side panels and said back side panels, to which the tab region is releasably attachable, has a stiffness, said second stiffness of said portion of the tab region of the respective tab being greater than said stiffness of said other one of said front side panels and said back side panels.

5. The absorbent article set forth in claim 1 wherein the tab region is releasably attachable to at least one of the inner layer and the outer layer of the central absorbent assembly, said at least one of the inner layer and the outer layer having a stiffness, said second stiffness of said portion of the tab region of the respective tab being greater than said stiffness of said at least one of the inner layer and the outer layer of the central absorbent assembly.

6. The absorbent article set forth in claim 1 wherein the outer layer has a stiffness, said second stiffness of said portion of the tab region of the respective tab being greater than said stiffness of the outer layer.

7. The absorbent article set forth in claim 1 wherein the inner layer has a stiffness, said second stiffness of said portion of the tab region of the respective tab being greater than said stiffness of the inner layer.

8. The absorbent article set forth in claim 1 wherein said second stiffness of said portion of the tab region of the respective tab has a stiffness value between about 10 milligrams and about 10,000 milligrams.

9. The absorbent article set forth in claim 8 wherein said second stiffness of said portion of the tab region of the respective tab has a stiffness value between about 10 milligrams and about 2,000 milligrams.

10. An absorbent article for personal wear about a wearer's waist, said article comprising:
    a liquid permeable bodyside liner for facing the wearer;

an outer cover for facing away from the wearer;

an absorbent body disposed between the liner and the outer cover;

a front waist region, a back waist region and a crotch region extending longitudinally between and interconnecting the front and back waist regions;

a pair of laterally opposite front side panels extending outward from the front waist region;

a pair of laterally opposite back side panels extending outward from the back waist region, the back side panels and front side panels cooperatively defining respective sides of the article, the sides of the article having a stiffness;

a primary fastening system for releasably attaching the front side panels directly to respective back side panels; and a secondary fastening system comprising a tab attached to one side of the article, the tab having a fastener region selectively attachable to the article, the tab having a stiffness that is greater than the stiffness of said one side of the article, the tab having an attachment region defining a portion of the primary fastening system.

11. The absorbent article set forth in claim 10 wherein the tab further comprises a grip region being generally non-attachable to the article at least in the wear configuration thereof for use in gripping the grip region of the tab.

12. The absorbent article set forth in claim 11 wherein the fastener region of the tab is releasable attachable to one of the front side panels and the back side panels.

13. The absorbent article set forth in claim 10 wherein the stiffness of the tab is at least 10 milligrams greater than the stiffness of the sides of the article.

14. The absorbent article set forth in claim 10 wherein the tab has a stiffness value between about 10 milligrams and about 10,000 milligrams.

15. The absorbent article set forth in claim 14 wherein the tab has a stiffness value between about 10 milligrams and about 2,000 milligrams.

16. An absorbent article for personal wear about a wearer's waist, said article comprising:

a liquid permeable bodyside liner for facing the wearer and having a stiffness;

an outer cover for facing away from the wearer and having a stiffness;

an absorbent body disposed between the liner and the outer cover;

a primary fastening system for securing the article in a wear configuration having a waist opening and a pair of leg openings spaced from the waist opening; and a secondary fastening system comprising a tab attached to the outer cover, the tab having a fastener region selectively attachable to the article, the tab having a stiffness that is greater than the stiffness of the outer cover, the tab having an attachment region defining a portion of the primary fastening system.

17. The absorbent article set forth in claim 16 wherein the stiffness of the tab is greater than the stiffness of the bodyside liner.

18. The absorbent article set forth in claim 16 wherein the tab further comprises a grip region being generally non-attachable to the article at least in the wear configuration for use in gripping the grip region of the tab.

19. The absorbent article set forth in claim 16 wherein the tab is attached to the outer cover.

20. The absorbent article set forth in claim 19 wherein the tab is attached on the outer cover such that, in the wear configuration, the tab is disposed between the waist opening and one of the leg openings.

\* \* \* \* \*